(12) United States Patent
Mowell et al.

(10) Patent No.: US 10,342,694 B1
(45) Date of Patent: Jul. 9, 2019

(54) DENTAL GUARD

(71) Applicant: Dentek Oral Care, Inc., Maryville, TN (US)

(72) Inventors: Eric W. Mowell, Maryville, TN (US); Geoffrey A. de Rohan, Knoxville, TN (US); Eric Matthew Krouse, Columbus, OH (US); Edward Michael Gandelman, Columbus, OH (US); James Huang Lua, Columbus, OH (US)

(73) Assignee: Dentek Oral Care, Inc., Maryville, TN (US)

( * ) Notice: Subject to any disclaimer, the term of this patent is extended or adjusted under 35 U.S.C. 154(b) by 1109 days.

(21) Appl. No.: 14/333,861

(22) Filed: Jul. 17, 2014

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ............ A63B 71/085; A63B 2071/086; A63B 2071/088; A63B 71/081; A63B 71/08–71/10; A61C 7/08; A61C 9/0006; A61C 19/063–19/066; A61C 9/00–9/0013; A61F 2005/563; A61F 5/566; A61F 5/56–5/58; A61M 16/0488–16/0497
See application file for complete search history.

(56) References Cited

U.S. PATENT DOCUMENTS

| | | | | |
|---|---|---|---|---|
| 5,297,960 A | * | 3/1994 | Burns ................. | A61C 9/0006 433/41 |
| 5,836,761 A | * | 11/1998 | Belvedere ............ | A63B 71/085 433/6 |
| 5,873,365 A | * | 2/1999 | Brown ...................... | A61F 5/56 128/859 |
| 5,938,435 A | * | 8/1999 | Raspino, Jr. ............. | A61C 7/12 433/2 |

(Continued)

*Primary Examiner* — Alireza Nia
*Assistant Examiner* — Michelle J Lee
(74) *Attorney, Agent, or Firm* — Taylor English Duma LLP

(57) ABSTRACT

A dental guard including a generally u-shaped band having a curved central portion and a pair of opposite aft ends, each of the aft ends of the band including a laterally extending cylindrical protrusion; and a pair of bite pad assemblies adjustably mountable onto the opposite aft ends of the band. Each of the bite pad assemblies includes a longitudinal channel configured for receiving one of the aft ends of the band for adjusting the location of the bite pad assembly on the band to adjust the length of the dental guard. Each of the bite pad assemblies also includes an elongate slot defined in a sidewall of the bite pad assembly adjacent to and open to the channel, the slot being configured to receive the laterally extending cylindrical protrusion of the aft end of the band and the slot including a plurality of spaced apart receivers for fixedly but releasably receiving the protrusion to enable adjustable positioning of the bite pad assembly relative to the aft end. The receivers are configured to enable the aft end of the band to pivot relative to the bite pad assembly when installed thereon to enhance fit of the dental guard to the user (Continued)

and optimize placement of the dental guard relative to a buccal side of the front teeth of the user.

7 Claims, 6 Drawing Sheets

(56)  References Cited

U.S. PATENT DOCUMENTS

| | | | |
|---|---|---|---|
| 6,152,138 | A | 11/2000 | Brown et al. |
| 7,490,609 | B2 | 2/2009 | Brown |
| D614,304 | S | 4/2010 | Jansheski |
| 7,832,404 | B2 | 11/2010 | Jansheski |
| 2009/0032030 | A1* | 2/2009 | Callender ............... A61F 5/566 128/845 |
| 2009/0159089 | A1* | 6/2009 | Jansheski ............... A61F 5/566 128/861 |
| 2010/0206314 | A1* | 8/2010 | Brown ................... A61F 5/566 128/861 |
| 2013/0327343 | A1* | 12/2013 | Cook ................... A63B 71/085 128/862 |

* cited by examiner

DENTAL GUARD

FIELD

The present disclosure relates to dental mouth guards. More particularly, the disclosure relates to dental guards configured for improved fit and comfort.

BACKGROUND

Improvement is desired in the construction of dental mouth guards of the type used in connection with bruxism, characterized by grinding of the teeth during sleep. Dental guards that are custom made for a user are expensive.

Off the shelf dental guards are available, but desire improvement in many respects. In particular, what is desired is an improved off the shelf type dental guard that is adjustable to fit a variety of users and provides improved comfort and fit.

SUMMARY

The disclosure advantageously provides a dental guard for positioning within a mouth of a user. The dental guards are particularly configured for inhibiting tooth grinding, such as bruxism.

In one aspect, the dental guard includes a generally u-shaped band having a curved central portion and a pair of opposite aft ends, each of the aft ends of the band including a laterally extending cylindrical protrusion; and a pair of bite pad assemblies adjustably mountable onto the opposite aft ends of the band.

Each of the bite pad assemblies includes a longitudinal channel configured for receiving one of the aft ends of the band for adjusting the location of the bite pad assembly on the band to adjust the length of the dental guard. Each of the bite pad assemblies also includes an elongate slot defined in a sidewall of the bite pad assembly adjacent to and open to the channel, the slot being configured to receive the laterally extending cylindrical protrusion of the aft end of the band and the slot including a plurality of spaced apart receivers for fixedly but releasably receiving the protrusion to enable adjustable positioning of the bite pad assembly relative to the aft end. The receivers are configured to enable the aft end of the band to pivot relative to the bite pad assembly when installed thereon to enhance fit of the dental guard to the user and optimize placement of the dental guard relative to a buccal side of the front teeth of the user.

In another aspect, the dental guard includes a generally u-shaped band having a curved central portion and a pair of opposite aft ends. The curved central portion of the u-shaped band is of reduced dimension as compared to the ends, and overmolded with a soft polymeric material to provide a cushion to help reduce irritation of the gums and lower lip of the user. A pair of bite pad assemblies are adjustably mountable onto the opposite aft ends of the band.

BRIEF DESCRIPTION OF THE DRAWINGS

Further advantages of the disclosure are apparent by reference to the detailed description when considered in conjunction with the figures, which are not to scale so as to more clearly show the details, and wherein.

DETAILED DESCRIPTION

Figure 1:
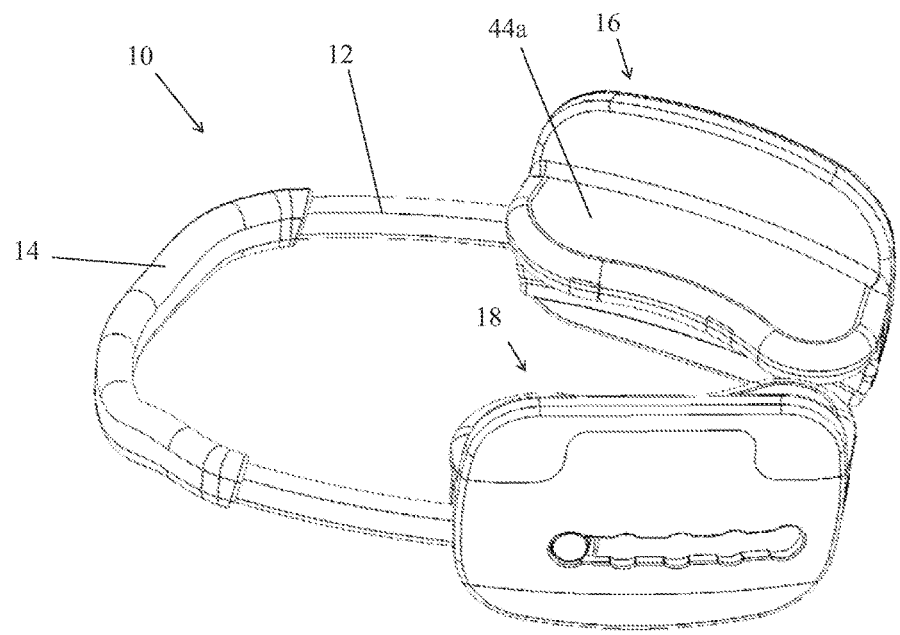
FIGS. 1 and 2 are perspective views of a dental guard according to the disclosure.
Figure 2:
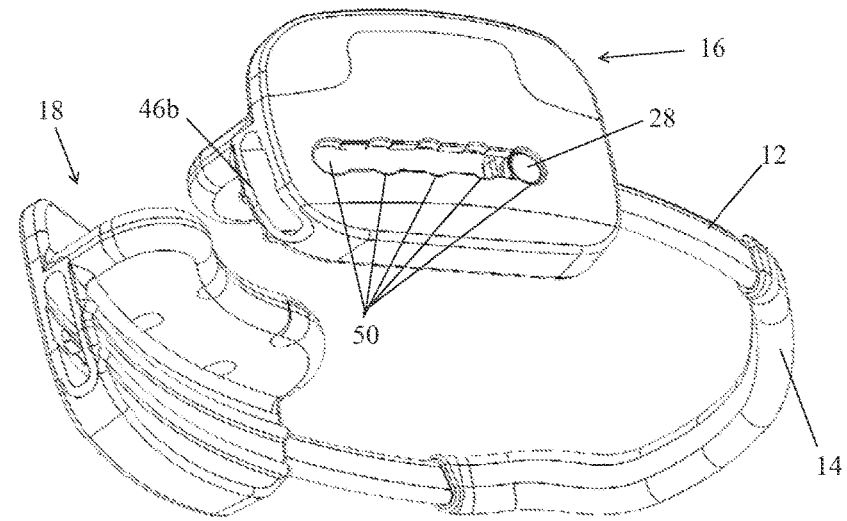
Figure 3:
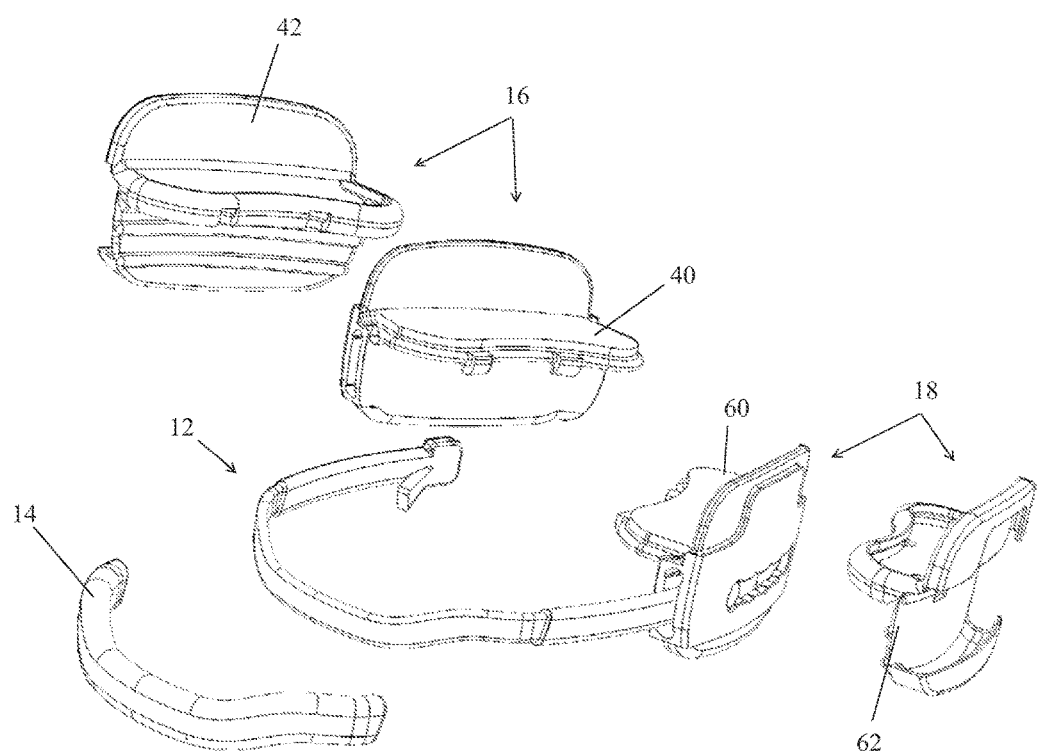
FIG. 3 is an exploded perspective view of the dental guard of FIGS. 1 and 2.
Figure 4:
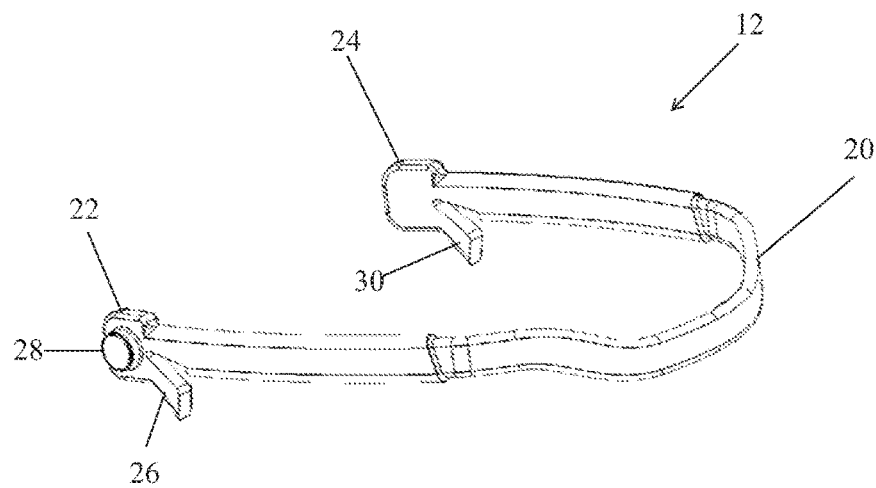
FIGS. 4 and 5 show a band component of the dental guard of FIGS. 1 and 2.
Figure 5:
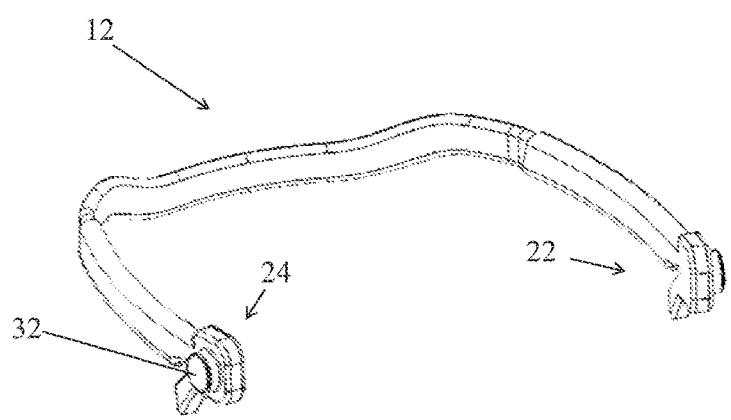
Figure 6:
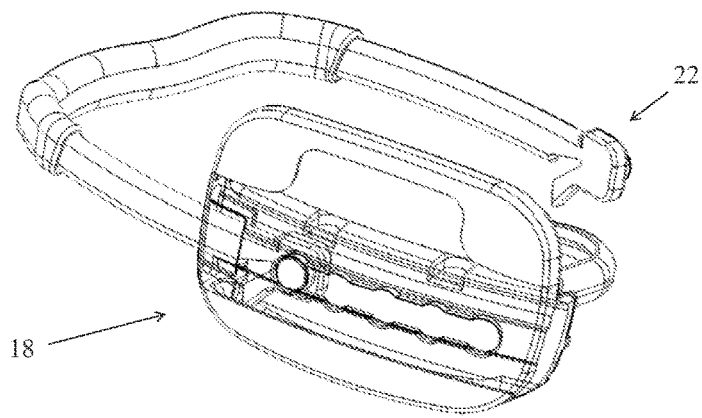
FIGS. 6 and 7 show a bite pad assembly installed onto the band component.
Figure 7:
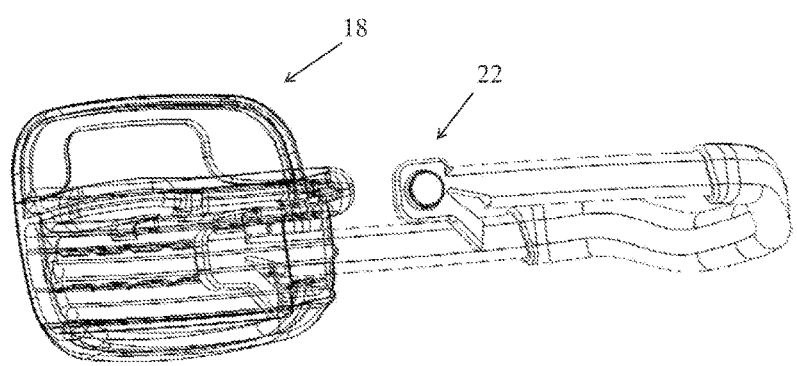
Figure 8:
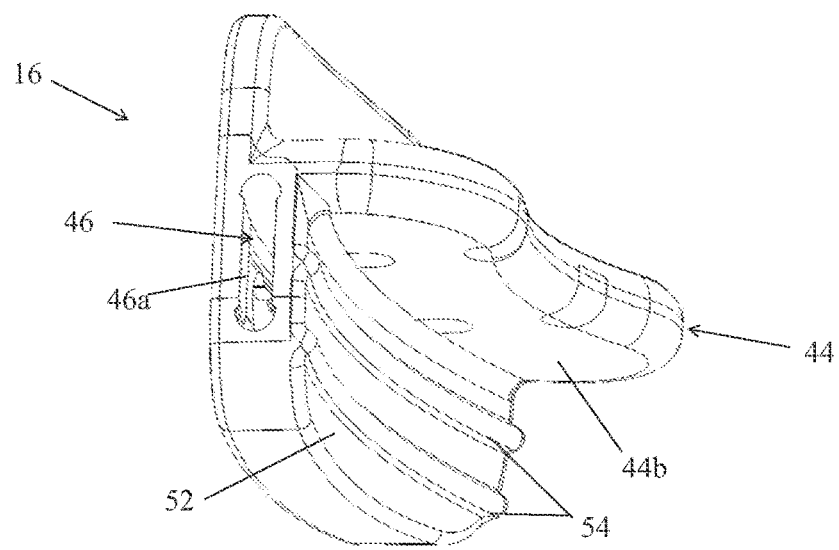
FIGS. 8 and 9 show a bite pad assembly of the dental guard of FIGS. 1 and 2.
Figure 9:
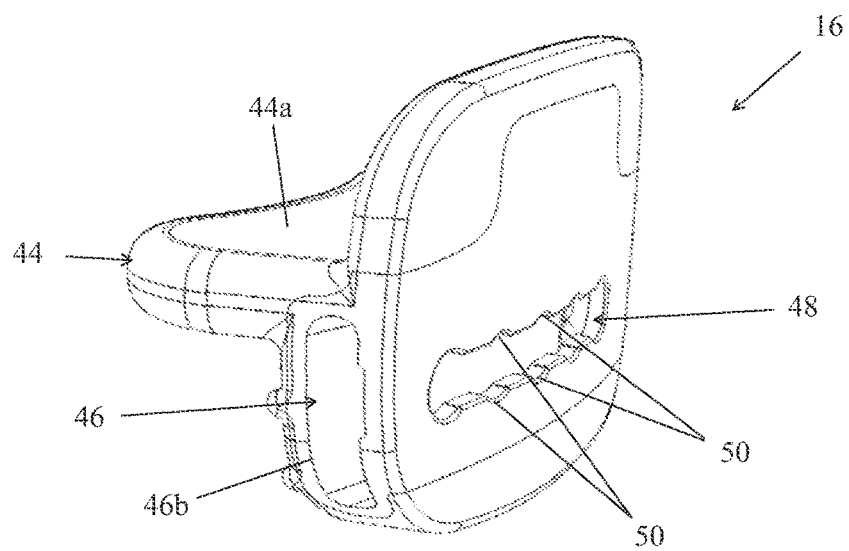
Figure 10:
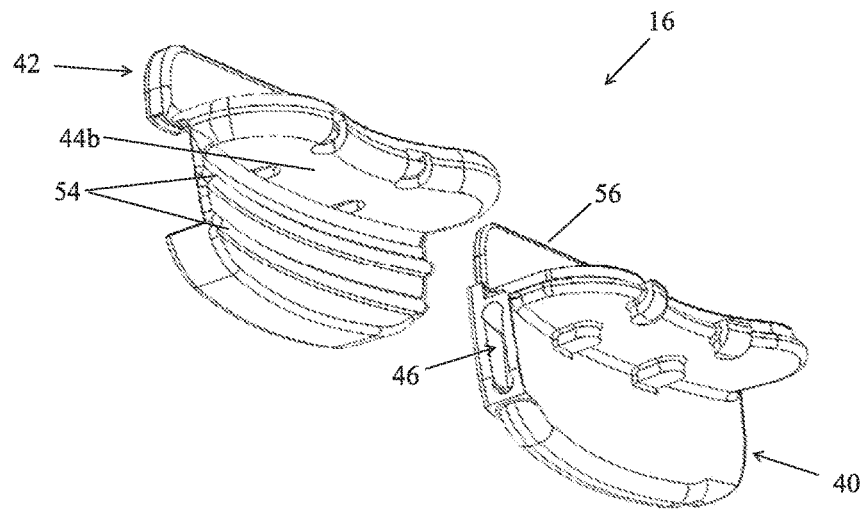
FIGS. 10 and 11 are exploded perspective views of the bite pad assembly of FIGS. 8 and 9.
Figure 11:
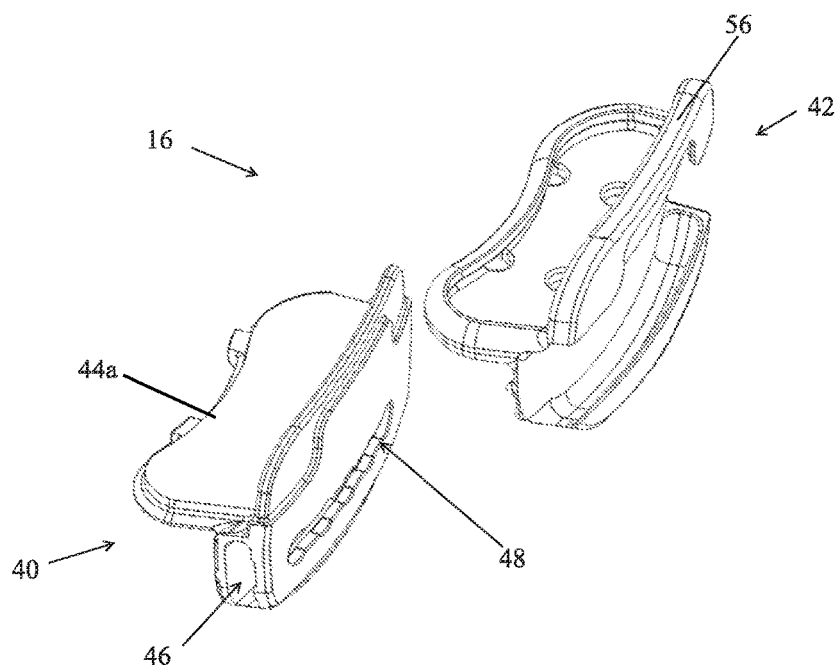

With reference to the drawings, the disclosure relates to a dental guard 10 including a band 12 having a cushion 14 mounted thereon, and a pair of bite pad assemblies 16 and 18 adjustably mountable onto opposite ends of the band 12.

The band 12 is generally u-shaped in configuration having a curved central portion 20 and a pair of aft ends 22 and 24. The band 12 is configured to be positioned in the mouth of the user so that the central curved portion 20 is located at the front of the mouth of a user, with the ends 22 and 24 located in the cheek sides of the mouth to position the bite pad assemblies 16 and 18 between upper and lower back teeth of the user. The band 12 may be made as by injection molding, and is made of a relatively hard and rigid polymeric or plastic material such as an ethylene vinyl acetate resin. The band 12 is desirably molded of ethyl methyl acrylate (EMA) to provide a desired hardness for interfacing with bite pad advancement. Other materials suitable for the band 12 include ethyl vinyl acetates (EVA) and blends thereof.

The central portion 20 may be of reduced dimension as compared to the ends 22 and 24. The central portion 20 may be overmolded with a softer polymeric material to provide the cushion 14 to help reduce irritation of the gums and lower lip of the user. A preferred material for overmolding the EMA material is EVA to provide a softer overmolded material. However, the overmolded material need not necessarily be softer. For example, if the nand 12 is made of EVA, then the overmolded material may be of the same material, or may have the same softness but less stiff (e.g., less tensile).

The end 22 includes a flexible finger 26 extending outwardly from the band 12. The finger 26 cooperates with the bite pad assembly 16 to enable installation of the bite pad assembly 16 onto the end 22. The finger 26 also serves to maintain the installed bite pad assembly 16 installed on the end 22 so that the bite pad assembly 16 does not detach from the band 12 during use of the dental guard 10. The end 22 also includes a laterally extending cylindrical protrusion 28 that cooperates with the bite pad assembly 16 to enable adjustable positioning of the bite pad assembly 16 relative to the end 22, and to permit the band 12 to pivot or rotate relative to the bite bad assembly 16.

The end 24 is configured in the same manner as the end 22, but as a mirror image on the opposite side of the band 12, and includes a corresponding flexible finger 30 and cylindrical protrusion 32 for cooperating with the bite pad assembly 18.

The bite pad assembly 16 includes a rigid frame 40 and a soft covering 42 formed onto portions of the frame 40. The rigid frame 40 may be made as by injection molding, and is made of a relatively hard and rigid polymeric or plastic material such as an EMA, although EVA and other materials may also be used. The soft covering 42 may be made as by overmolding onto the frame 40 with a softer polymeric material. In this manner the bite pad assembly 16 is configured to provide a bite pad 44 having a relatively hard upper pad surface 44a made of the harder polymeric material and a relatively soft lower pad surface 44b made of the softer polymeric material. The benefit of the composite bite pad structure is that the softer lower pad surface 44b enables the lower teeth of the user to grip the bite pad 44 while the harder upper pad surface 44a permits the upper teeth of the user to slide freely over the bite pad 44 when the teeth of the user impart a grinding action to the bite pad 44 such as a grinding action associated with bruxism. Thus, the composite bite pad 44 serves to cushion the teeth, separates the lower and upper teeth from contacting one another, while enabling the jaw of the user to move without interference from the dental guard 10.

In addition to having the bite pad 44, the bite pad assembly 16 also includes a longitudinal open-ended through channel 46. The channel 46 is defined by the rigid frame 40 and configured for receiving the aft end 20 of the band 12 for adjusting the location of the bite pad assembly 16 on the band 12 to adjust the length of the dental guard 10 to fit a variety of mouth sizes.

For example, an elongate slot 48 is defined in a sidewall of the frame 40 adjacent to and open to the channel 46 and facing the cheek of the user (opposite the teeth). The slot 48 is configured to receive the laterally extending cylindrical protrusion 28 of the aft end 22 of the band 12. In this regard, the slot 48 permits travel of the protrusion 28 and includes a plurality of preferably uniformly spaced apart receivers 50 for fixedly but releasably receiving the protrusion 28 to enable adjustable positioning of the bite pad assembly 16 relative to the end 22. That is, each receiver 50 designates an incremental adjustment size to which the bite pad assembly 16 may be adjusted. The receivers 50 are preferably circular to match the cylindrical protrusion to enable the aft end 22 of the band 12 to pivot relative to the bite pad assembly 16. This freedom to pivot enhances the fit of the dental guard 10 to the user and optimizes placement of the dental guard 10 relative to the buccal or cheek side of the front teeth of the user.

In addition, the engagement of the finger 26 with the interior of the channel 46 prevents the bite pad assembly 16 from being completely removed from band 12. During initial assembly of the dental guard 10, the finger 26 deflects sufficiently downward to allow the end 22 of the band 12 to be inserted into and slide through a forward opening 46a of the channel 46, and the finger 26 also serves to prevent the end 22 from a rear opening 46b of the channel 46. Thus, after initial assembly, the end 22 of the band 12 is always contained within the bite pad assembly 16.

The composite structure of the bite pad assembly 16 also provides improved comfort features for the dental guard 10. For example, a lower buccal sidewall 52 provided by the soft covering 42 includes a plurality of raised ribs or bumps 54 configured to slightly push off the teeth. The bumps 54 are advantageous to reduce contact between the lower buccal sidewall 52 of the bite pad assembly 16 and the gums of the lower teeth of the user. The soft covering 42 also advantageously provides soft surfaces at the edges, including the corners of the bite pad assembly 16 to reduce gum irritation. Additional comfort features are provided by the frame 40 having an upper buccal sidewall 56 of reduced thickness to enable improved fit and to accommodate the slight offset between the upper teeth and the lower teeth of a typical user.

The bite pad assembly 18 is configured in the same manner as the bite pad assembly 16, but as a mirror image and is configured to seat on the end 24 of the band 12. Thus, the bite pad assembly 18 includes a corresponding rigid frame 60 and a soft covering 62 formed onto portions of the frame 60.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A dental guard for positioning within a mouth of a user, the dental guard comprising:
    a u-shaped band having a curved central portion and a pair of opposite aft ends, each of the aft ends of the band including a laterally extending cylindrical protrusion; and
    a pair of bite pad assemblies adjustably mountable onto the opposite aft ends of the band, each of the bite pad assemblies including a longitudinal channel configured for receiving one of the aft ends of the band for adjusting a location of the bite pad assembly on the band to adjust a length of the dental guard, each of the bite pad assemblies also including an elongate slot defined in a sidewall of the bite pad assembly adjacent to and open to the channel, the slot being configured to receive the laterally extending cylindrical protrusion of the aft end of the band and the slot including a plurality of spaced apart receivers for fixedly but releasably receiving the protrusion to enable adjustable positioning of the bite pad assembly relative to the aft end, the receivers each being configured to enable the aft end of the band to pivot relative to the bite pad assembly when installed thereon to enhance fit of the dental guard to the user and optimize placement of the dental guard relative to a buccal side of the front teeth of the user.

2. The dental guard of claim 1, wherein each of the bite pad assemblies includes a frame made of a first polymeric material having a first hardness, and a covering made of a second polymeric material overmolded onto the frame, the covering having a second hardness that is softer than the first hardness.

3. The dental guard of claim 2, wherein each of the bite pad assemblies includes a bite pad, with an upper surface of the bite pad configured for contacting upper teeth of the user provided by the first polymeric material, and a lower surface of the bite pad configured for contacting lower teeth of the user coated with the second polymeric material.

4. The dental guard of claim 2, wherein each of the bite pad assemblies includes a lower buccal sidewall provided by the covering and including a plurality of raised surfaces configured to slightly push off lower teeth of the user and reduce contact between the lower buccal sidewall of the bite pad assembly and gums portions of the lower teeth of the user.

5. The dental guard of claim 1, wherein the curved central portion of the u-shaped band is of reduced dimension as compared to the ends, and is overmolded with a soft polymeric material to provide a cushion to help reduce irritation of the gums and lower lip of the user.

6. The dental guard of claim 1, further comprising a flexible finger on each of the aft ends of the band and configured for being received within the channels, the flexible fingers being configured to prevent removal of the received aft ends of the band from the channels.

7. A dental guard, comprising:

a u-shaped band having a curved central portion and a pair of opposite aft ends, each of the aft ends of the band defining a flexible finger and a laterally extending protrusion;

a pair of bite pad assemblies adjustably mountable onto the opposite aft ends of the band, each of the bite pad assemblies including a longitudinal channel configured for receiving one of the aft ends of the band for adjusting a location of the bite pad assembly on the band to adjust a length of the dental guard, with the flexible finger of each aft end configured to be received into the channel preventing removal of the received aft end from the channel, each of the bite pad assemblies also including an elongate slot defined in a sidewall of the bite pad assembly adjacent to and open to the channel, the slot being configured to receive the laterally extending protrusion of the aft end of the band, and the slot including a plurality of spaced apart receivers for fixedly but releasably receiving the protrusion to enable adjustable positioning of the bite pad assembly relative to the aft end, the receivers each being configured to enable the aft end of the band to pivot relative to the bite pad assembly when installed thereon to enhance fit of the dental guard to a user and optimize placement of the dental guard relative to a buccal side of the front teeth of the user.

\* \* \* \* \*